United States Patent
Heo et al.

(10) Patent No.: US 11,432,774 B2
(45) Date of Patent: Sep. 6, 2022

(54) PULSE OXIMETERS AND PULSE OXIMETER EMBEDDED ORGANIC IMAGE SENSORS

(71) Applicant: Samsung Electronics Co., Ltd., Suwon-si (KR)

(72) Inventors: Chui Joon Heo, Busan (KR); Kyung Bae Park, Hwaseong-si (KR); Dongseon Lee, Suwon-si (KR); Moon Gyu Han, Suwon-si (KR); Takkyun Ro, Hwaseong-si (KR); Youn Hee Lim, Suwon-si (KR); Yong Wan Jin, Seoul (KR); Kiyohiko Tsutsumi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 486 days.

(21) Appl. No.: 16/255,981

(22) Filed: Jan. 24, 2019

(65) Prior Publication Data

US 2019/0239821 A1    Aug. 8, 2019

(30) Foreign Application Priority Data

Feb. 5, 2018    (KR) .................. 10-2018-0014255

(51) Int. Cl.
*A61B 5/00* (2006.01)
*A61B 5/1455* (2006.01)
(Continued)

(52) U.S. Cl.
CPC .......... *A61B 5/7278* (2013.01); *A61B 5/0205* (2013.01); *A61B 5/02416* (2013.01);
(Continued)

(58) Field of Classification Search
CPC .............. A61B 5/7278; A61B 5/02416; A61B 5/14551; A61B 5/02427; A61B 5/0205;
(Continued)

(56) References Cited

U.S. PATENT DOCUMENTS

2007/0075252 A1    4/2007 Misawa
2010/0234706 A1*   9/2010 Gilland .............. A61B 5/14552
                                                           600/344
(Continued)

FOREIGN PATENT DOCUMENTS

KR    20170044826 A    4/2017
WO    WO-2016066312 A1    5/2016

OTHER PUBLICATIONS

Lochner et al. Nature Communications—All-organic optoelectronic sensor for pulse oximetry. Article published, Dec. 10, 2014, pp. 1-7.
(Continued)

*Primary Examiner* — Allen Porter
*Assistant Examiner* — Abid A Mustansir
(74) *Attorney, Agent, or Firm* — Harness, Dickey & Pierce, P.L.C.

(57) ABSTRACT

A pulse oximeter may include a photoelectric conversion device having wavelength selectivity so that a low output LED may be included in the pulse oximeter to prevent skin damage and to reduce power consumption. The pulse oximeter includes a light emitting device configured to emit white light and a sensor configured to detect transmitted light that is received from the light emitting device. The sensor includes a near infrared organic photoelectric conversion device configured to sense a particular near infrared wavelength spectrum of light and a red photoelectric conversion device configured to sense a particular red wavelength spectrum of light.

13 Claims, 9 Drawing Sheets

(51) Int. Cl.
  *H01L 27/30* (2006.01)
  *A61B 5/024* (2006.01)
  *A61B 5/0205* (2006.01)
  *H01L 51/42* (2006.01)
  *A61B 5/02* (2006.01)
  *H01L 27/146* (2006.01)

(52) U.S. Cl.
  CPC ...... *A61B 5/02427* (2013.01); *A61B 5/14551* (2013.01); *A61B 5/14552* (2013.01); *A61B 5/6801* (2013.01); *A61B 5/6898* (2013.01); *A61B 5/742* (2013.01); *H01L 27/307* (2013.01); *A61B 5/02007* (2013.01); *A61B 5/02433* (2013.01); *A61B 5/6833* (2013.01); *A61B 2562/046* (2013.01); *A61B 2576/00* (2013.01); *H01L 27/14645* (2013.01); *H01L 27/14669* (2013.01); *H01L 51/42* (2013.01); *H01L 51/4206* (2013.01)

(58) Field of Classification Search
  CPC ..... A61B 5/6801; A61B 5/742; A61B 5/6898; A61B 2576/00; A61B 5/02007; A61B 5/6833; A61B 5/145; H01L 27/307; H01L 51/42
  See application file for complete search history.

(56) References Cited

U.S. PATENT DOCUMENTS

| 2012/0136227 | A1 | 5/2012 | McKenna |
| 2015/0105633 | A1* | 4/2015 | LeBoeuf .............. A61B 5/0261 600/301 |
| 2017/0055907 | A1 | 3/2017 | Altebaeumer et al. |
| 2017/0078513 | A1* | 3/2017 | Chang ..................... H04N 1/10 |

OTHER PUBLICATIONS

Extended European Search Report dated Jun. 18, 2019 for corresponding European Application No. 19154795.9.
Office Action dated Mar. 28, 2022 issued in corresponding Korean patent application No. 10-2018-0014255.

* cited by examiner

PULSE OXIMETERS AND PULSE OXIMETER EMBEDDED ORGANIC IMAGE SENSORS

CROSS-REFERENCE TO RELATED APPLICATION

This application claims priority to and the benefit of, under 35 U.S.C. § 119, Korean Patent Application No. 10-2018-0014255 filed in the Korean Intellectual Property Office on Feb. 5, 2018, the entire contents of which are incorporated herein by reference.

BACKGROUND

1. Field

The present disclosure relates to pulse oximeters and pulse oximeter-embedded near infrared organic image sensors.

2. Description of the Related Art

According to the increasing human life-span, it has been considered important to develop smart health-care sensors which may periodically and concisely check a variety of biometric signals or health information in daily life, without having to visit a medical center.

Recently, a function to sense and monitor biometric data has been added to accessories such as smart phones and/or smart bands, and ways to variously utilize the biometric data have been steadily researched. In some cases, conventional large-scale medical equipment for measuring and collecting concise biometric data may be down-sized, but performance of the medical equipment has to be maintained regardless of the downsizing.

A pulse oximeter may sense both a heart rate and oxygen saturation of blood at the same time in a non-invasive way, and has a merit of downsizing, so it has been employed for many products. If information (e.g., biometric data) of the heart rate and the oxygen saturation of blood is easily measured and accumulated, it may be usefully utilized for preventing a disease based on health data such as that of a circulatory system and pulmonary function. The conventional pulse oximeter generally includes two LEDs and one photodiode. The LED is selected to have a selective light emitting characteristic of a narrow width in each wavelength of a red region and a green region, each LED is caused to emit light in one cycle, and an optical signal obtained in a photodiode based on transmission of the emitted light through a blood vessel and to the photodiode is analyzed to determine heart rate and oxygen saturation.

Recently, various attempts to provide a flexible pulse oximeter have been performed for applying the same to a portable accessory. (KR2017-0044826 or All-organic optoelectronic sensor for pulse oximetry, Lochner, C. M. et al., Nature Comm., 5, 5745 (2014))

However, a photodiode used for the pulse oximeter which has been developed so far depends upon wavelength separation of an LED light source.

Particularly, to compensate for the use of a photodiode having insufficient sensitivity and to obtain a concise optical signal from light transmitted through skin and passed through a blood vessel, the intensity of the light source should be sufficient. However, such a light source may cause burning of skin or damage to tissue of patients or subjects based on emitting light having sufficient intensity to enable the photodiode to obtain a concise optical signal based on the light being transmitted through skin and passed through a blood vessel and further to the photodiode.

In addition, the conventional medical sensors, as disclosed in KR2017-0044826, use a lead wire which is not flexible, so a life-span of the sensor is determined by the same.

SUMMARY

Pulse oximeters employing a photoelectric conversion device having wavelength selectivity re provided, so a low output LED may be employed for preventing skin damage and reducing power consumption of the pulse oximeters.

The pulse oximeters may be sufficiently downsized to be applicable for a portable device.

The pulse oximeters may be formed with ("may at least partially comprise") an organic material, so they may be provided in a wearable manner.

Pulse oximeter-embedded near infrared organic image sensors which may be mounted in a variety of portable devices such as a smart phone are provided.

A pulse oximeter according to some example embodiments includes a light emitting device emitting white light, and a near infrared organic photoelectric conversion device and a red photoelectric conversion device detecting transmitted light and reflected light in the light emitting device after irradiating to a blood vessel.

A pulse oximeter-embedded near infrared organic image sensor according to some example embodiments includes an inorganic red photoelectric conversion device formed in a semiconductor substrate, and a near infrared organic photoelectric conversion device including a near infrared organic photoelectric conversion layer formed in the semiconductor substrate, a common electrode on the near infrared organic photoelectric conversion layer, and a pixel electrode under the organic photoelectric conversion layer, wherein the inorganic red photoelectric conversion device and the near infrared organic photoelectric conversion device detect transmitted light and reflected light after irradiating to a blood vessel.

According to some example embodiments, by employing the photoelectric conversion device having wavelength selectivity, a low output LED may be employed for preventing skin damage and reducing power consumption.

It may be sufficiently downsized to be applicable for a portable device.

It is formed with an organic material, so may be provided in a wearable device.

The pulse oximeter may be embedded in an image sensor for a variety of portable devices such as a smart phone.

According to some example embodiments, a pulse oximeter may include a light emitting device configured to emit white light to irradiate a blood vessel, and a sensor configured to detect transmitted light that is received from the light emitting device, subsequently to the transmitted light having irradiated the blood vessel. The sensor may include a near infrared organic photoelectric conversion device configured to sense a particular near infrared wavelength spectrum of light, and a red photoelectric conversion device configured to sense a particular red wavelength spectrum of light.

The light emitting device may be configured to emit white light having an intensity of about 1 to about 10 mW.

The red photoelectric conversion device may be an organic red photoelectric conversion device. The organic red photoelectric conversion device may be between a semiconductor substrate and the near infrared organic photoelectric conversion device.

The red photoelectric conversion device may be an inorganic red photoelectric conversion device embedded in a semiconductor substrate.

The inorganic red photoelectric conversion device may include an array of a plurality of inorganic red photoelectric conversion elements. Each inorganic red photoelectric conversion element of the plurality of inorganic red photoelectric conversion elements may define a separate unit pixel.

The pulse oximeter may further include a signal processor configured to calculate a heart rate and oxygen saturation based on a determination of an absorbance of near infrared light that is measured by the near infrared organic photoelectric conversion device based on at least a portion of the transmitted light in the particular near infrared wavelength spectrum being absorbed by the near infrared organic photoelectric conversion device, and an absorbance of red light that is measured by the red photoelectric conversion device based on at least a portion of the transmitted light in the particular red wavelength spectrum being absorbed by the red photoelectric conversion device.

According to some example embodiments, a pulse oximeter-embedded near infrared organic image sensor may include an inorganic red photoelectric conversion device embedded in a semiconductor substrate. The inorganic red photoelectric conversion device may be configured to sense a particular red wavelength spectrum of light. The pulse oximeter-embedded near infrared organic image sensor may include a near infrared organic photoelectric conversion device including a near infrared organic photoelectric conversion layer on the semiconductor substrate. The near infrared organic photoelectric conversion layer may be configured to sense a particular near infrared wavelength spectrum of light, a common electrode on the near infrared organic photoelectric conversion layer, and a pixel electrode between the near infrared organic photoelectric conversion layer and the semiconductor substrate. The inorganic red photoelectric conversion device and the near infrared organic photoelectric conversion device may be configured to detect light received from a light emitting device subsequently to the light irradiating a blood vessel.

The inorganic red photoelectric conversion device may include an array of a plurality of inorganic red photoelectric conversion devices, and each inorganic red photoelectric conversion device of the plurality of inorganic red photoelectric conversion devices may define a separate unit pixel.

The pulse oximeter-embedded near infrared organic image sensor may further include an inorganic blue photoelectric conversion device and an inorganic green photoelectric conversion device embedded in the semiconductor substrate.

The pulse oximeter-embedded near infrared organic image sensor may further include a signal processor configured to calculate a heart rate and oxygen saturation using an absorbance of near infrared light that is measured by the near infrared organic photoelectric conversion device based on at least a portion of the received light in the particular near infrared wavelength spectrum being absorbed by the near infrared organic photoelectric conversion device, and an absorbance of red light that is measured by the inorganic red photoelectric conversion device based on at least a portion of the received light in the particular red wavelength spectrum being absorbed by the inorganic red photoelectric conversion device.

According to some example embodiments, a wearable pulse oximeter may include a light emitting device configured to emit white light; and a sensor including a stack of a near infrared organic photoelectric conversion device and a red organic photoelectric conversion device. The near infrared organic photoelectric conversion device may be configured to sense a particular near infrared wavelength spectrum of light. The red photoelectric conversion device may be configured to sense a particular red wavelength spectrum of light.

The wearable pulse oximeter may further include a signal processor configured to calculate a heart rate and oxygen saturation using an absorbance of near infrared light that is measured by the near infrared organic photoelectric conversion device based on at least a portion of incident light in the particular near infrared wavelength spectrum being absorbed by the near infrared organic photoelectric conversion device, and an absorbance of red light that is measured by the red photoelectric conversion device based on at least a portion of the incident light in the particular red wavelength spectrum being absorbed by the red photoelectric conversion device.

The wearable pulse oximeter may further include a flexible display configured to display a signal of the sensor.

According to some example embodiments, an angiographic device may include a light emitting device configured to emit white light to irradiate a blood vessel, an array of a plurality of inorganic red photoelectric conversion devices embedded in a semiconductor substrate, wherein each inorganic red photoelectric conversion device defines a separate unit pixel, and a near infrared organic photoelectric conversion device including a near infrared organic photoelectric conversion layer on the semiconductor substrate, a common electrode on the near infrared organic photoelectric conversion layer, and a pixel electrode between the near infrared organic photoelectric conversion layer and the semiconductor substrate. The inorganic red photoelectric conversion device may be configured to sense a particular red wavelength spectrum of light of transmitted light that is received from the light emitting device, subsequently to the transmitted light having irradiated the blood vessel, and the near infrared organic photoelectric conversion device is configured to sense a particular near infrared wavelength spectrum of light of the transmitted light.

The angiographic device may further include a signal processor configured to calculate a heart rate and oxygen saturation using an absorbance of near infrared light that is measured by the near infrared organic photoelectric conversion device based on at least a portion of the transmitted light in the particular near infrared wavelength spectrum being absorbed by the near infrared organic photoelectric conversion device, and an absorbance of red light that is measured by the red photoelectric conversion device based on at least a portion of the transmitted light in the particular red wavelength spectrum being absorbed by the red photoelectric conversion device.

According to some example embodiments, a smart phone may include a light emitting device configured to emit white light to irradiate a blood vessel, and a pulse oximeter-embedded near infrared organic image sensor configured to detect transmitted light transmitted from the light emitting device, subsequently to the transmitted light having irradiated the blood vessel. The sensor may include an inorganic red photoelectric conversion device embedded in a semiconductor substrate, the inorganic red photoelectric conversion device configured to sense a particular red wavelength spectrum of light, a near infrared organic photoelectric conversion layer on the semiconductor substrate, the near infrared organic photoelectric conversion layer configured to absorb a particular near infrared wavelength spectrum of light, a common electrode on the near infrared organic photoelectric conversion layer, and a pixel electrode between the near infrared organic photoelectric conversion layer and the semiconductor substrate.

The smart phone may further include an inorganic blue photoelectric conversion device and an inorganic green photoelectric conversion device embedded in the semiconductor substrate.

The smart phone may further include a signal processor configured to calculate a heart rate and oxygen saturation using an absorbance of near infrared light that is measured by the sensor based on at least a portion of the transmitted light in the particular near infrared wavelength spectrum being absorbed by the near infrared organic photoelectric conversion layer, and an absorbance of red light that is measured by the sensor based on at least a portion of the transmitted light in the particular red wavelength spectrum being absorbed by the inorganic red photoelectric conversion device.

According to some example embodiments, a pulse oximeter may include a light emitting device configured to emit white light, and a sensor configured to detect a particular limited wavelength portion of the white light that is emitted by the light emitting device. The sensor may include a near infrared organic photoelectric conversion device configured to sense a particular near infrared wavelength spectrum of light, and a red photoelectric conversion device configured to sense a particular red wavelength spectrum of light.

The red photoelectric conversion device may be between the near infrared organic photoelectric conversion device and a semiconductor substrate.

The pulse oximeter may further include a signal processor configured to calculate a heart rate and oxygen saturation based on a determination of an absorbance of near infrared light that is measured by the near infrared organic photoelectric conversion device based on at least a portion of the white light that is emitted by the light emitting device in the particular near infrared wavelength spectrum being absorbed by the near infrared organic photoelectric conversion device, and an absorbance of red light that is measured by the red photoelectric conversion device based on at least a portion of the white light that is emitted by the light emitting device in the particular red wavelength spectrum being absorbed by the red photoelectric conversion device.

DETAILED DESCRIPTION

Hereinafter, the present disclosure will be described more fully with reference to the accompanying drawings, in which some example embodiments of the disclosure are shown. As those skilled in the art would realize, the described embodiments may be modified in various different ways, all without departing from the spirit or scope of the present disclosure.

Figure 1:
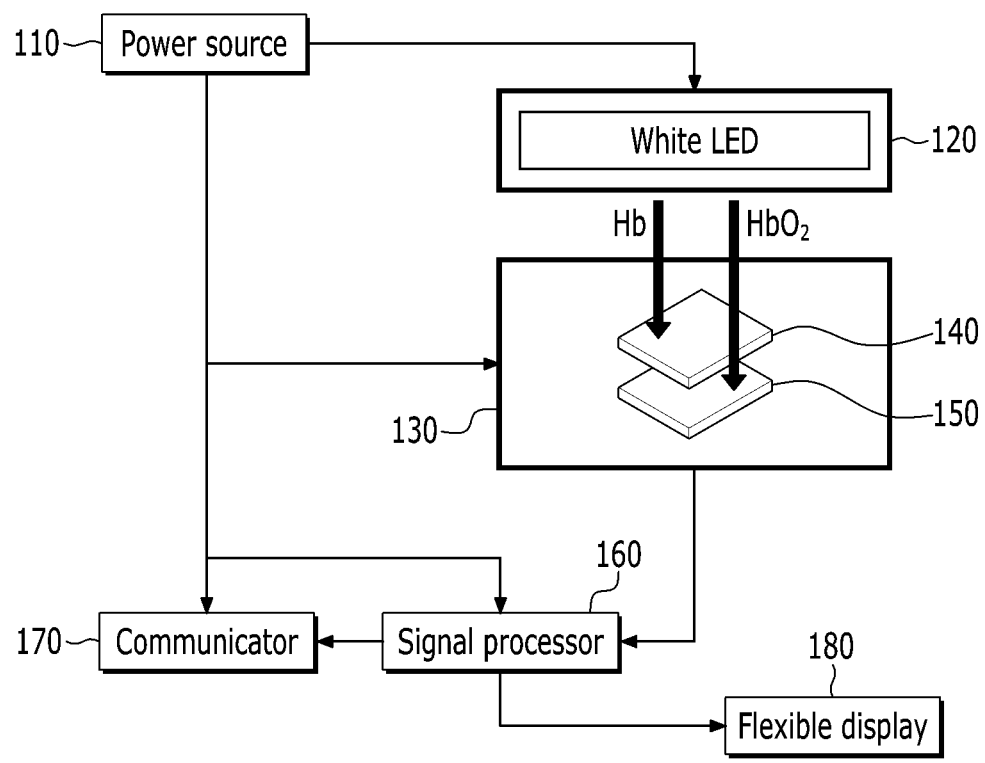
FIG. 1 is a schematic view showing a pulse oximeter according to some example embodiments of the present inventive concepts.

FIG. 1 is a schematic view showing a pulse oximeter according to some example embodiments of the present inventive concepts.

Referring to FIG. 1, the pulse oximeter 1 includes a power source 110, a light emitting device 120, a sensor 130, a signal processor 160, and a communication interface device 170.

The power source 110 supplies power to the light emitting device 120, the sensor 130, the signal processor 160, and the communication interface device 170, and it may be provided as an ultra-small battery or a flexible battery and the like in a case of a portable device.

The light emitting device 120 may be provided as one white light emitting diode (LED) only. As referred to herein, a white LED may be configured to emit "white light," where "white light" may be understood to be light that is a combination of light of different wavelengths in the visible wavelength spectrum (between about 400 nm and about 780 nm). For example, white light may include a combination of "red light," "green light," and "blue light," where red light includes light in a red wavelength spectrum of about 625 nm to about 780 nm, green light includes light in a green wavelength spectrum of about 495 nm to about 570 nm, and blue light includes light in a blue wavelength spectrum of about 450 nm to about 495 nm. The white LED may either be an inorganic LED or an organic LED, but the organic LED may be more appropriate to accomplish a flexible device. As the conventional pulse oximeter uses only a photodiode having no wavelength selectivity, the wavelength of emitted light may be divided in the light emitting device 120. As a result, the light emitting device 120 includes an LED having a light emitting characteristic selective to a red region ("red wavelength spectrum") and an LED having a light emitting characteristic selective to a near infrared region ("near infrared wavelength spectrum") or a green region ("green wavelength spectrum"), and in order to compensate the sensitivity of the insufficiently sensitive photodiode, the light intensity of the light source may be increased up to around 10-30 mW to emit light, which may result in tissue damage (e.g., skin damage) based on the intensity of the emitted light passing through human tissue. However, in the pulse oximeter according to some example embodiments of the present disclosure, the sensor 130, which is described later, has wavelength selectivity (e.g., is configured to sense light in one or more particular limited wavelength spectra), so it is sufficient for the light emitting device 120 to include only a white LED configured to emit white light, and it is also sufficient to emit the white light of the white LED light source of a low intensity of about 1-10 mW, which is sufficiently low intensity of emitted white light to at least partially mitigate the risk of tissue damage resulting from the emitted white light passing through human tissue and/or a blood vessel to reach the sensor 130. Additionally, because the white LED may only emit white light at a lower intensity of about 1-10 mW, power consumption of the pulse oximeter 1 may be reduced without reducing capability of the device to implement pulse oximetry, thereby improving performance of the device.

When the terms "around," "about," or "substantially" are used in this specification in connection with a numerical value, it is intended that the associated numerical value include a tolerance of ±10% around the stated numerical value. When ranges are specified, the range includes all values therebetween such as increments of 0.1%.

Figure 2:
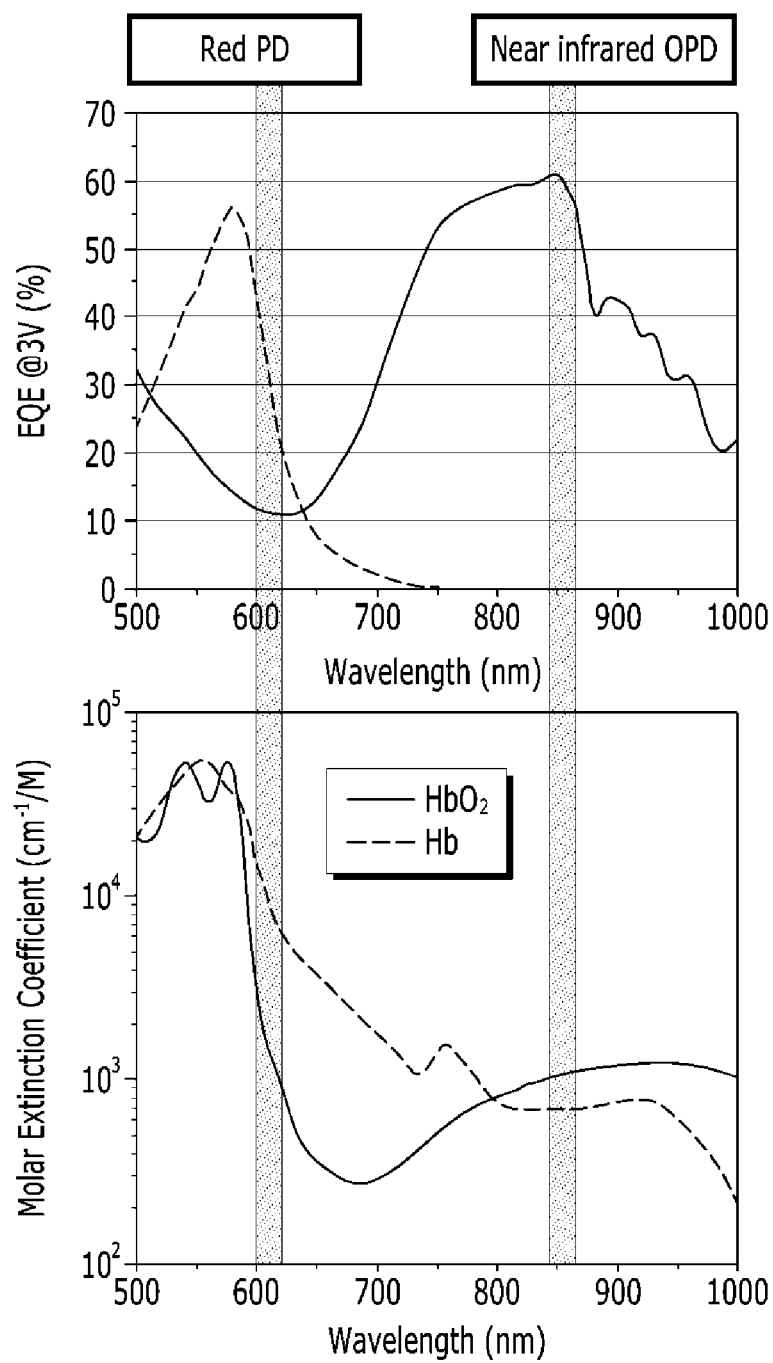
FIG. 2 is a graph showing external quantum efficiency (EQE) characteristics of a red photoelectric conversion device and a near infrared organic photoelectric conversion device, and extinction coefficients of oxyhemoglobin (HbO2) and deoxyhemoglobin (Hb) in a red wavelength and a near infrared wavelength.

The sensor 130 includes a near infrared organic photoelectric conversion device 140 and a red photoelectric conversion device 150. The sensor 130 is configured to detect transmitted light, of the white light that is emitted by the light emitting device 120, subsequently to the transmitted light having irradiated a blood vessel. As shown in FIG. 2, the near organic photoelectric conversion device 140 is configured to sense and/or absorb light in a particular, limited, near infrared wavelength spectrum 142 (e.g., "near infrared light"), and the red photoelectric conversion device 150 is configured to sense and/or absorb light in a particular, limited, red wavelength spectrum 152 (e.g., "red light"), such that the sensor 130 is configured to have wavelength selectivity so it is sufficient for the light emitting device 120 to include only a white LED configured to emit white light, and it is also sufficient to emit the white light of the white LED light source of a low intensity of about 1-10 mW. As shown in FIG. 1, the near infrared organic photoelectric conversion device 140 may be proximate to an incident light side 156 of the sensor 130, such that incident light that is incident on the sensor 130 via the incident light side 156 must pass through the near infrared organic photoelectric conversion device 140 to be incident on the red photoelectric conversion device 150. The red photoelectric conversion device 150 may be between the near infrared organic photoelectric conversion device 140 and a substrate 158. In some example embodiments, the near infrared organic photoelectric conversion device 140 may be between the red photoelectric conversion device 150 and the incident light side 156 of the sensor 130. In some example embodiments, the red photoelectric conversion device 150 may be between the near infrared organic photoelectric conversion device 140 and the incident light side 156 of the sensor 130.

Referring to FIG. 2, the external quantum efficiency (EQE) of the near infrared organic photoelectric conversion device 140 is relatively high in the near infrared wavelength spectrum 142 of light that the near infrared organic photoelectric conversion device 140 is configured to sense and/or absorb, and the external quantum efficiency of the red photoelectric conversion device 150 is relatively high in the red wavelength spectrum 152 of light that the red photoelectric conversion device 150 is configured to sense (e.g., absorb). Meanwhile, looking at the molar extinction coefficient of oxyhemoglobin (HbO2) and deoxyhemoglobin (Hb), the oxyhemoglobin (HbO2) has a relatively higher molecule extinction coefficient than the deoxyhemoglobin (Hb) in the near infrared ray region (e.g., near infrared wavelength spectrum 142), and the deoxyhemoglobin (Hb) has a relatively higher extinction coefficient than the oxyhemoglobin (HbO2) in the red wavelength spectrum 152.

Accordingly, referring to FIG. 1 again, the signal processor 160 may calculate a Hb/HbO2 concentration ratio based on an absorbance of near infrared light (e.g., light in the near infrared wavelength spectrum 142) that is measured by the near infrared organic photoelectric conversion device 140 of the sensor 130 based on at least a portion of incident light (e.g., transmitted light that is emitted by the light emitting device 120 and irradiates a blood vessel and is subsequently received by the sensor 130) in the particular near infrared wavelength spectrum (e.g., wavelength spectrum 142) being absorbed by the near infrared organic photoelectric conversion device 140 and an absorbance of red light (e.g., light in the red wavelength spectrum 152) that is measured by the red photoelectric conversion device 150 of the sensor 130 based on at least a portion of incident light (e.g., transmitted light that is emitted by the light emitting device 120 and irradiates a blood vessel and is subsequently received by the sensor 130) in the particular red wavelength spectrum (e.g., wavelength spectrum 152) being absorbed by the red photoelectric conversion device 150, and may then calculate oxygen saturation using the same. In addition, the signal processor 160 may calculate a heart rate through a waveform shown in the measurement.

The signal digitalized in the signal processor 160 may transmit the measured oxygen saturation and pulse signals to an external remote processing device (ex., a smart phone, a remote monitoring device, etc.) through the communication interface device 170. The communication interface device 170 may communicate by wire, or may communicate by near field wireless communication such as Bluetooth, Zig-Bee, UWB (Ultra Wide Band), IEEE 802.11 based Wi-Fi, and the like.

As shown in FIG. 1, the near infrared organic photoelectric conversion device 140 and the red photoelectric conversion device 150 for the sensor 130 may be laminated. In some example embodiments, the red photoelectric conversion device 150 may also be formed of ("may at least partially comprise") an organic material as is the near infrared organic photoelectric conversion device 140. When the photoelectric conversion devices 140 and 150 are formed only of organic materials as above, it is easy for them to be fabricated with a flexible substrate. Accordingly, it may be applicable for a wearable pulse oximeter such as a disposable or patch-type pulse oximeter. In some example embodiments, a flexible display 180 may also be mounted in the pulse oximeter so that the results are directly shown without transmitting the same to an external display through the communication interface device 170. Restated, the flexible display 180 may be configured to display a signal of the sensor 130.

Figure 3:
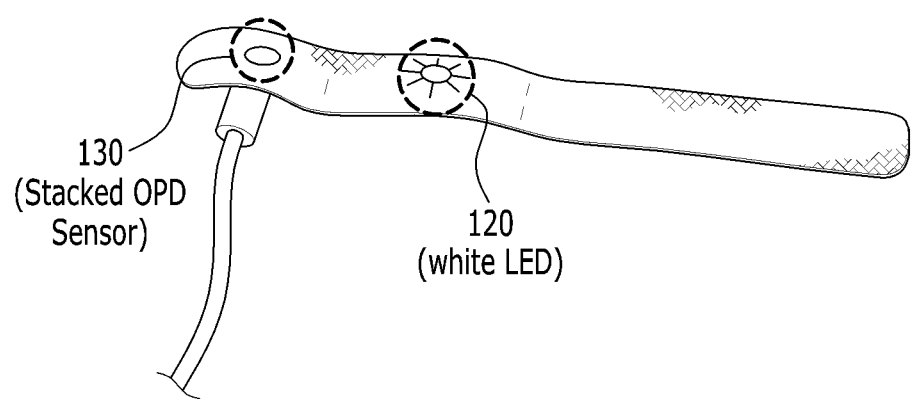
FIG. 3 shows a patch-type pulse oximeter employing a pulse oximeter according to some example embodiments of the present inventive concepts.

FIG. 3 is a schematic view showing a patch-type pulse oximeter 300 embodying a pulse oximeter 1 according to some example embodiments of the present inventive concepts. The pulse oximeter 1 shown in FIG. 3 may be the pulse oximeter 1 shown in FIG. 1. The patch-type pulse oximeter 300 may be a wearable pulse oximeter that includes a wearable strap 320 that is configured to be attached to a portion of a human body, and wherein one or more portions of the pulse oximeter 1 are incorporated into the wearable strap 320.

The pulse oximeter 1 may include a white LED 120 and a sensor 130 in which a near infrared organic photoelectric conversion device 140 and a red organic photoelectric conversion device 150 are stacked on a patch-type flexible substrate 158. Accordingly, it will be understood that the sensor 130 may include a "stack" of a near infrared organic photoelectric conversion device 140 and a red organic photoelectric conversion device 150. When the signal measured by the sensor 130 is transmitted via a wire 310 as shown in FIG. 3, the signal processor 160 or the communication interface device 170 may be omitted from the pulse oximeter 1 shown in FIG. 1.

As shown in FIG. 1, the red organic photoelectric conversion device 150 may be between the near infrared organic photoelectric conversion device 140 and a semiconductor substrate 158, such that the red organic photoelectric conversion device 150 is distal from a light incident side of the sensor 130 in relation to the near infrared organic photoelectric conversion device 140, but example embodiments are not limited thereto. For example, in some example embodiments, the near infrared organic photoelectric conversion device 140 may be between the red organic photoelectric conversion device 150 and a substrate 158, such that the near infrared organic photoelectric conversion device 140 is distal from a light incident side of the sensor 130 in relation to the red organic photoelectric conversion device 150.

Figure 4:
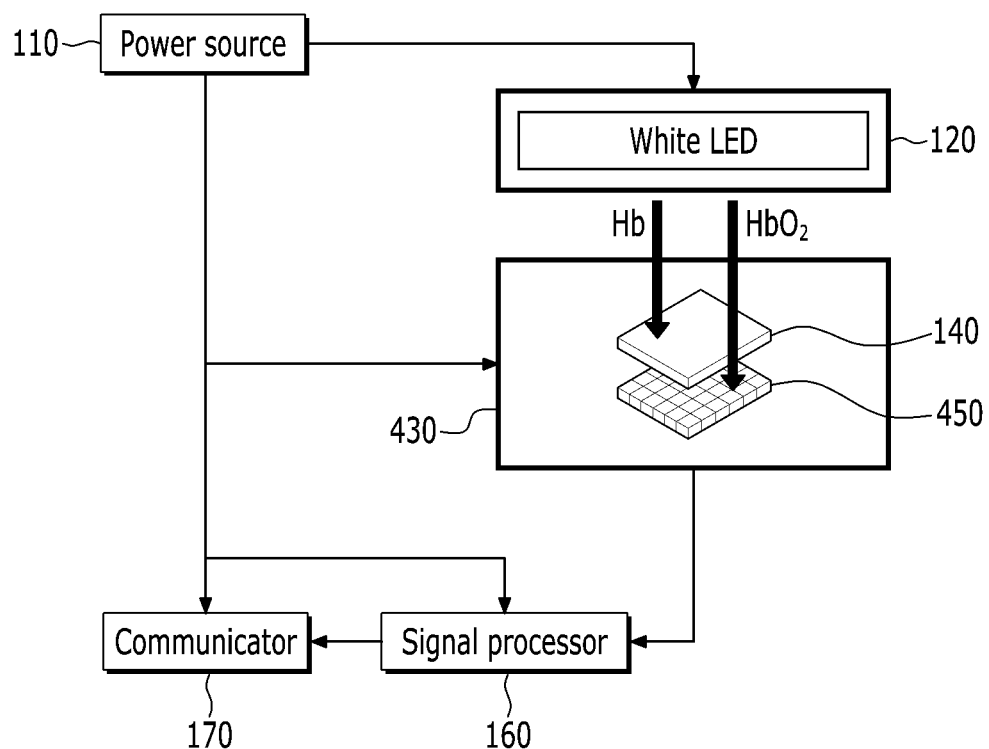
FIG. 4 is a schematic view showing a pulse oximeter according to some example embodiments of the present inventive concepts.

FIG. 4 shows a pulse oximeter according to some example embodiments of the present disclosure. Referring to FIG. 4, unlike the sensor 130 of the pulse oximeter shown in FIG. 1, the sensor 430 includes a near infrared organic photoelectric conversion device 140 and an inorganic red photoelectric conversion device 450 under the same (e.g., between the near infrared organic photoelectric conversion device 140 and a substrate). The lower inorganic red photoelectric conversion device 450 may be at least partially formed in (e.g., embedded in) a semiconductor substrate, for example, a silicon substrate, such that the lower inorganic red photoelectric conversion device 450 is at least partially located within a volume that is defined by outer surfaces of the semiconductor substrate. The inorganic red photoelectric conversion device 450 includes an array of a plurality of inorganic red photoelectric conversion devices, and each inorganic red photoelectric conversion device 450 may define a separate unit pixel PX. In some example embodiments, the near infrared organic photoelectric conversion device 140 may be between the inorganic red organic photoelectric conversion device 450 and a substrate, such that the near infrared organic photoelectric conversion device 140 is distal from a light incident side of the sensor 130 in relation to the inorganic red organic photoelectric conversion device 450.

When the lower inorganic red photoelectric conversion device 450 is formed with an array of a plurality of red pixels, it may provide the heart rate and the oxygen saturation for the subject with pixelated information. Restated, the inorganic red photoelectric conversion device 450 may include an array of a plurality of inorganic red photoelectric conversion elements 451-1 to 451-N (N being a positive integer), and each inorganic red photoelectric conversion element (also referred to herein as a inorganic red photoelectric conversion device) of the plurality of inorganic red photoelectric conversion elements 451-1 to 451-N may define a separate unit pixel PX. In some example embodiments, it may be applicable for a pulse oximeter and a camera for a medical purpose such as a surgery, so as to provide information on blood flow trouble and a damage condition of a certain blood vessel in the surgical site through concise pulse mapping. In addition, it may help to prevent additional damage of a region that is not yet damaged through a high resolution image of a blood vessel. Furthermore, by using the high resolution high efficient stacked pulse oximeter, it may be applied for an angiography apparatus ("angiographic device") configured to diagnose and treat with a laser through precise blood vessel imaging even without surgery.

Figure 5:
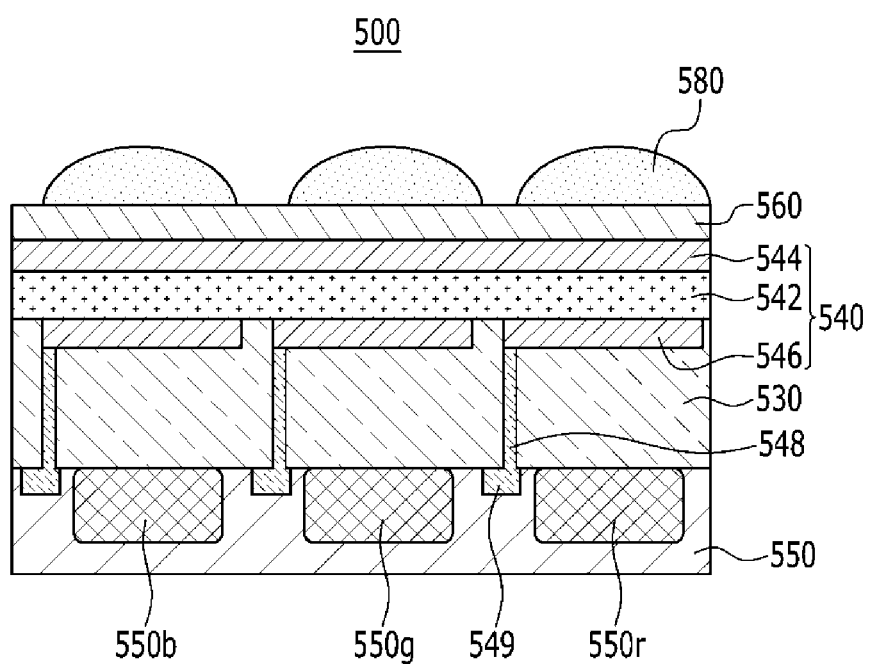
FIG. 5 is a schematic view showing a pulse oximeter-embedded near infrared organic image sensor according to some example embodiments of the present inventive concepts.
Figure 6:
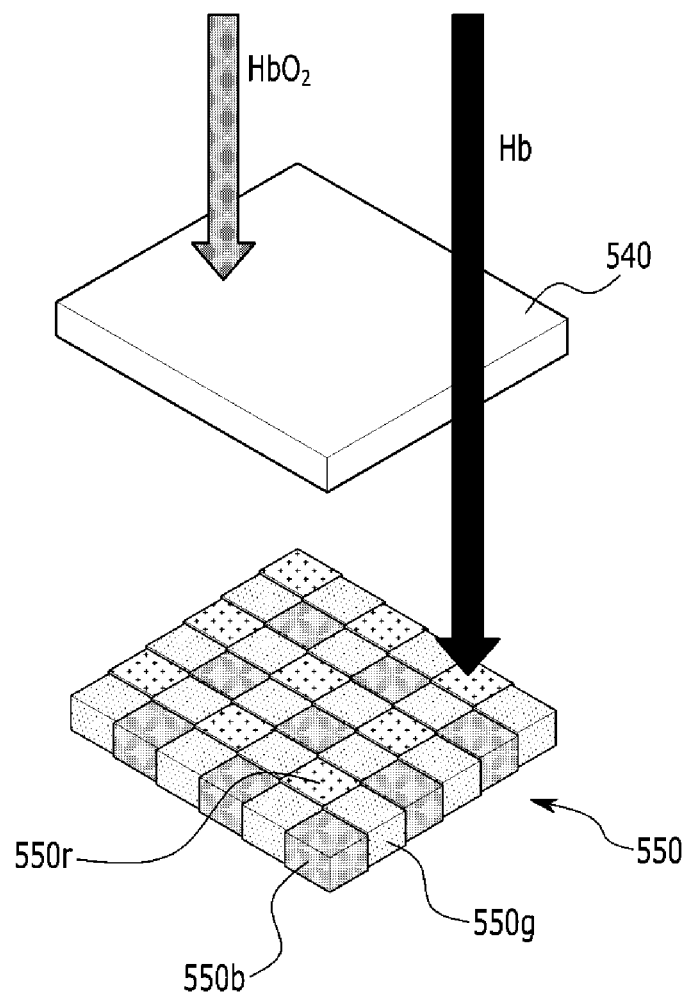
FIG. 6 is a schematic view showing a pixel array of a pulse oximeter-embedded near infrared organic image sensor according to still some example embodiments of the present inventive concepts.

FIG. 5 is a schematic view showing a pulse oximeter-embodied image sensor 500 according to some example embodiments of the present disclosure, and FIG. 6 is a schematic view showing a pixel array of the pulse oximeter-embodied image sensor 500.

Referring to FIGS. 5 and 6, the image sensor 500 includes an inorganic photoelectric conversion device 551 that includes an array of photoelectric conversion devices 550r, 550g, and 550b formed in ("embedded in") a semiconductor substrate 550, such that the photoelectric conversion devices 550r, 550g, and 550b are located within a volume space that is defined by the semiconductor substrate 550, as shown in at least FIG. 5, and a near infrared organic photoelectric conversion device 540 formed thereon ("on the array of photoelectric conversion devices 550r, 550g, and 550b").

The plurality of inorganic photoelectric conversion devices are formed with particular (or, alternatively, predetermined) alignment in a particular (or, alternatively, predetermined) region of the semiconductor substrate 550. The inorganic photoelectric conversion device 551 may include a red photoelectric conversion device 550r, a green photoelectric conversion device 550g, and a blue photoelectric conversion device 550b. It will be understood that, just as a red photoelectric conversion device 550r is configured to selectively absorb light having a red wavelength spectrum ("red light"), the green photoelectric conversion device 550g, and the blue photoelectric conversion device 550b are configured to selectively absorb light having a green wavelength spectrum ("green light") and light having a blue wavelength spectrum ("blue light"), respectively.

In some example embodiments, including the example embodiments shown in FIG. 6, the red photoelectric conversion device 550r, the green photoelectric conversion device 550g, and the blue photoelectric conversion device 550b may be disposed as a Bayer array, but of course the alignment may be variously changed.

The near infrared organic photoelectric conversion device 540 is formed of a combination of a near infrared organic photoelectric conversion layer 542 on the semiconductor substrate 550 and a common electrode 544 disposed on the near infrared organic photoelectric conversion layer 542, and a pixel electrode 546 formed for each separate pixel under the same such that each pixel electrode 546 is between the near infrared organic photoelectric conversion layer 542 and the semiconductor substrate 550 and, as shown in FIG. 5, each separate unit pixel PX of the image sensor 500 includes a separate photoelectric conversion device 550r, 550g, 550r and a separate pixel electrode 546 overlapped with a separate portion of the near infrared organic photoelectric conversion layer 542 and the common electrode 544. The near infrared organic photoelectric conversion layer 542 may be configured to absorb the particular near infrared wavelength spectrum 142. Each pixel electrode 546 is connected with a charge accumulator 549 through a contact 548 filled in a via formed in an interlayer insulating layer 530.

A flat layer 560 that is transparent to incident light is formed on the common electrode 544. A microlens 580 is formed to focus the incident light onto each pixel in a site corresponding to each pixel. As shown in FIG. 5, side 501A of the image sensor 500 may be a light incident side, such that the near infrared organic photoelectric conversion device 540 is proximate to the light incident side 501A in relation to the array of photoelectric conversion devices 550r, 550g, and 550b. But, in some example embodiments, side 501B of the image sensor 500 may be a light incident side, such that the near infrared organic photoelectric conversion device 540 is distal to the light incident side 501B in relation to the array of photoelectric conversion devices 550r, 550g, and 550b.

Figure 7:
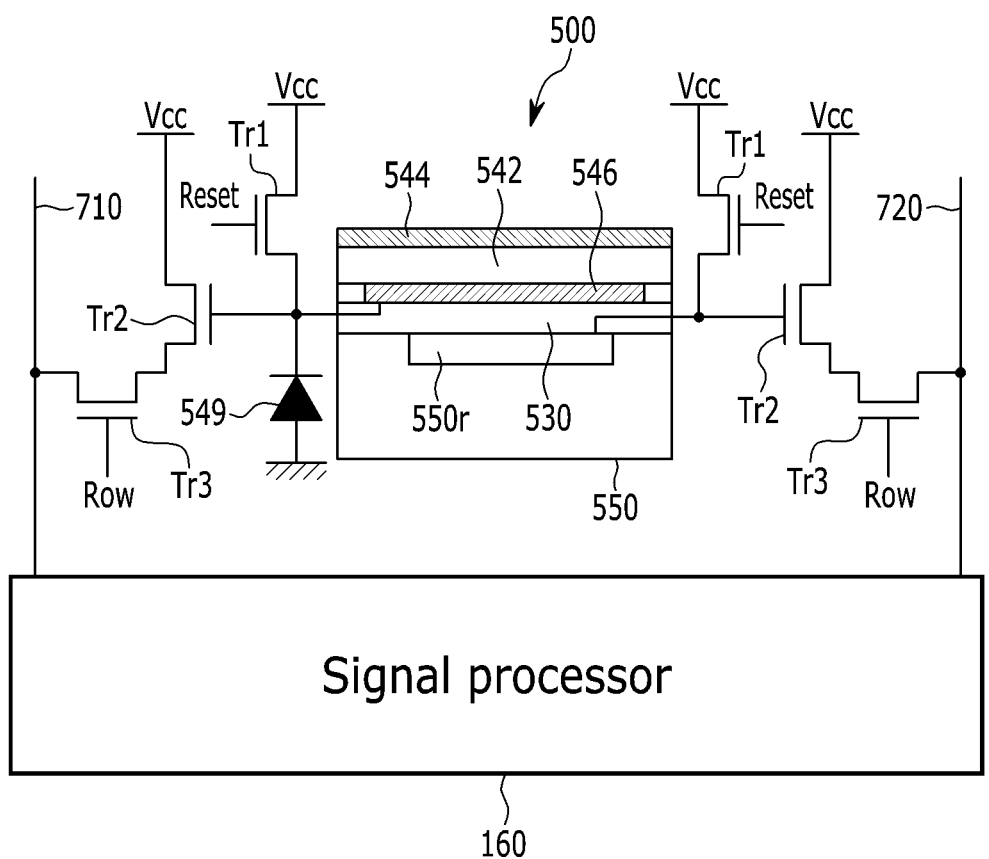
FIG. 7 is a schematic view showing a readout circuit of the pulse oximeter-embedded image sensor according to some example embodiments of the present inventive concepts.

FIG. 7 is a schematic view showing a readout circuit of the pulse oximeter-embedded image sensor 500 according to some example embodiments.

A charge accumulated in the inorganic photoelectric conversion devices 550r, 550g, and 550b and a charge accumulated in the charge accumulator 549 are sensed using a readout circuit including a transistor having a 3-transistor structure or a 4-transistor structure, and the like. FIG. 7 shows an example of an inorganic red photoelectric conversion device 550r, but it is equivalently applicable to an inorganic green photoelectric conversion device 550g and an inorganic blue photoelectric conversion device 550b.

Referring to FIG. 7, a charge accumulated in the inorganic red photoelectric conversion device 550r is read out by a reset transistor Tr1 having a drain connected to the inorganic red photoelectric conversion device 550r and a source connected to a power source Vn, an output transistor Tr2 having a gate connected to the drain of the reset transistor Tr1 and a source connected to the power source Vcc, and a row selective transistor Tr3 having a source connected to the drain of the output transistor Tr2 and a drain connected to the signal output line 720.

The charge detected by the near infrared organic photoelectric conversion device 540 and accumulated in the charge accumulator 549 is read out by a reset transistor Tr1 having a drain connected to the charge accumulator 549 and a source connected to a power source Vcc, an output transistor Tr2 having a gate connected to the drain of the reset transistor Tr1 and a source connected to the power source Vcc, and a row selective transistor Tr3 having a source connected to the drain of the output transistor Tr2 and a drain connected to the signal output line 710.

A charge generated and stored in the inorganic red photoelectric conversion device 550r is converted to a signal corresponded to an amount of charge through an output transistor Tr2. When the row selective transistor Tr3 is turned on, the signal is output to the signal output line 720. After outputting the signal, the charge of the inorganic red photoelectric conversion device 550r is reset by the reset transistor Tr1. If required, it may further include a delivering transistor (not shown) between the inorganic red photoelectric conversion device 550r and the drain of the reset transistor Tr1.

When a bias voltage is applied between the pixel electrode 546 and the common electrode 544, a charge is generated corresponding to light having entered the near infrared organic photoelectric conversion layer 542 and is transported to the charge accumulator 549 through a contact 548 connected with the pixel electrode 546. The charge stored in the charge accumulator 549 is converted to a signal corresponding to an amount of charge through the output transistor Tr2. When the row selective transistor Tr3 is turned on, the signal is output to the signal output line 710. After outputting the signal, the charge of the charge accumulator 549 is reset by the reset transistor Tr1. If required, it may further include a delivery transistor (not shown) between the charge accumulator 549 and the drain of the reset transistor Tr1.

The signal output through the two signal output lines 710 and 720 is transmitted to a signal processor 160, and a heart rate and oxygen saturation are calculated based on the data transmitted from the signal processor 160. The operation corresponds to a case of a pulse oximetry mode. In a case of a camera mode, all signals of the inorganic red photoelectric conversion device 550r, the inorganic blue photoelectric conversion device 550b, the inorganic green photoelectric conversion device 550g, and the signal of the near infrared organic photoelectric conversion device 540 are output, and an image signal may be finally output from the signal processor 160. Needless to say, the two modes may be simultaneously performed, if required.

When using the pulse oximeter-embedded image sensor 500 shown in FIGS. 5 and 6, it has a merit of simultaneously or selectively performing a camera mode using a general image sensor and the pulse oximetry mode. In other words, as required, only the camera mode may be operated, only the pulse oximeter may be operated, or both the camera mode and the pulse oximetry mode may be simultaneously operated.

Figure 8:
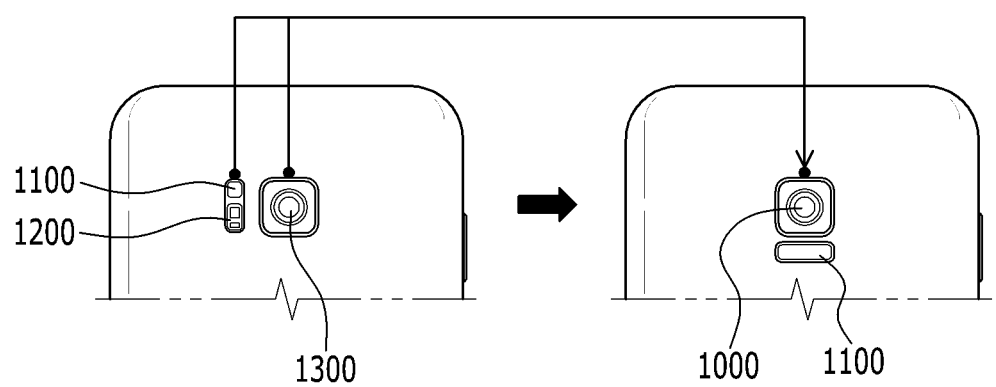
FIG. 8 is a pulse oximeter and a rear camera which used to be separately mounted in a mobile device according to some example embodiments of the present inventive concepts.

Thus as shown in FIG. 8, the pulse oximeter 1200 and a rear camera 1300, which used to be separately mounted in a mobile device 800A such as a smart phone, may be integrated into one camera 1000. It may further include a light emitting device 1100 on one side of the camera 1000 of a mobile device 800B such as a smart phone, so as to emit white light and to irradiate the same to a blood vessel.

Figure 9:
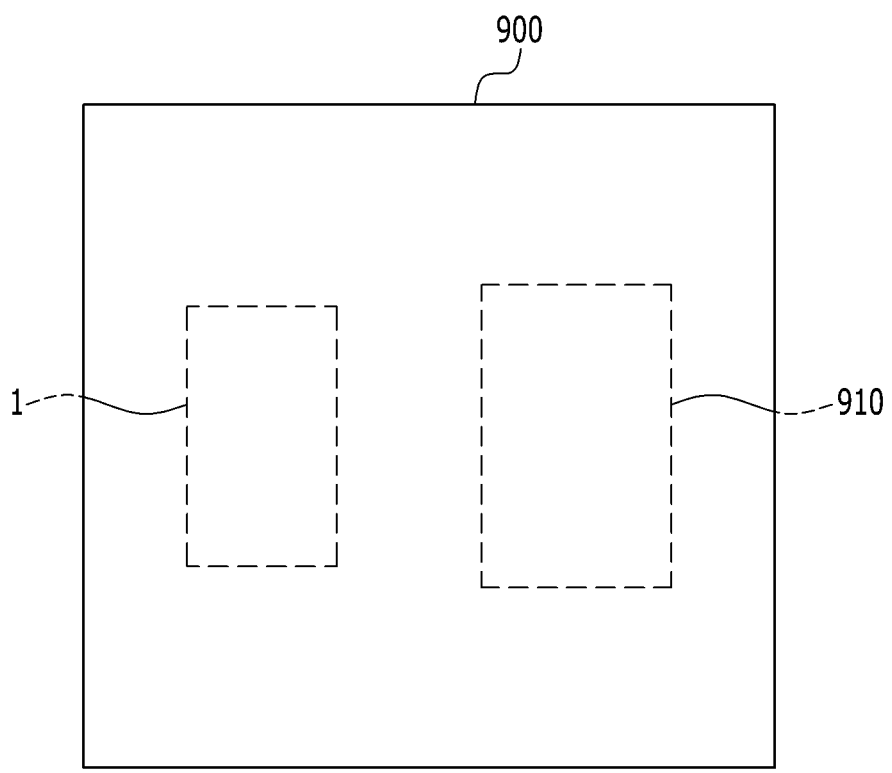
FIG. 9 is an angiographic device according to some example embodiments of the present inventive concepts.

FIG. 9 is an angiographic device according to some example embodiments of the present inventive concepts. The angiographic device 900 shown in FIG. 9 includes a pulse oximeter 1, which may be any of the example embodiments of pulse oximeters described herein. In some example embodiments, the angiographic device 900 includes a laser emitter device 910 that is configured to laser provide treatment to a blood vessel based on imaging provided by the pulse oximeter 1 even without surgery.

While this disclosure has been described in connection with what is presently considered to be practical some example embodiments, it is to be understood that the inventive concepts is not limited to the disclosed embodiments, but, on the contrary, is intended to cover various modifications and equivalent arrangements included within the spirit and scope of the appended claims.

DESCRIPTION OF SYMBOLS

110: power source
120: light emitting device
130: sensor
140: near infrared organic photoelectric conversion device
150: red photoelectric conversion device
160: signal processor
170: communication interface device

What is claimed is:
1. A pulse oximeter, comprising:
a light emitting device configured to emit white light having an intensity of about 1 to about 10 mW to irradiate a blood vessel; and
a sensor configured to detect transmitted light that is received from the light emitting device, subsequently to the transmitted light having irradiated the blood vessel, the sensor including a near infrared organic photoelectric conversion device on a semiconductor substrate, the near infrared organic photoelectric conversion device configured to sense a particular near infrared wavelength spectrum of light, and an array of inorganic photoelectric conversion devices embedded in the semiconductor substrate, the array of inorganic photoelectric conversion devices including a red inorganic photoelectric conversion device configured to sense a particular red wavelength spectrum of light, a blue inorganic photoelectric conversion device configured to sense a particular blue wavelength spectrum of light, and a green inorganic photoelectric conversion device configured to sense a particular green wavelength spectrum of light, wherein each separate inorganic photoelectric conversion device of the array of inorganic photoelectric conversion devices is overlapped with a separate portion of the near infrared organic photoelectric conversion device.

2. The pulse oximeter of claim 1, further comprising:

a signal processor configured to calculate a heart rate and oxygen saturation based on a determination of an absorbance of near infrared light that is measured by the near infrared organic photoelectric conversion device based on at least a portion of the transmitted light in the particular near infrared wavelength spectrum being absorbed by the near infrared organic photoelectric conversion device, and an absorbance of red light that is measured by the red inorganic photoelectric conversion device based on at least a portion of the transmitted light in the particular red wavelength spectrum being absorbed by the red inorganic photoelectric conversion device.

3. A pulse oximeter-embedded near infrared organic image sensor, comprising:

an array of inorganic photoelectric conversion devices embedded in a semiconductor substrate and at least partially defining a plurality of unit pixels, the array of inorganic photoelectric conversion devices including a plurality of inorganic red photoelectric conversion devices configured to sense a particular red wavelength spectrum of light, a plurality of inorganic blue photoelectric conversion devices configured to sense a particular blue wavelength spectrum of light, and a plurality of inorganic green photoelectric conversion devices configured to sense a particular green wavelength spectrum of light; and a near infrared organic photoelectric conversion device on the array of inorganic photoelectric conversion devices embedded in the semiconductor substrate, the near infrared organic photoelectric conversion device including a near infrared organic photoelectric conversion layer on the semiconductor substrate, the near infrared organic photoelectric conversion layer configured to sense a particular near infrared wavelength spectrum of light, a common electrode on the near infrared organic photoelectric conversion layer, and an array of pixel electrodes between the near infrared organic photoelectric conversion layer and the semiconductor substrate, wherein the plurality of inorganic red photoelectric conversion devices and the near infrared organic photoelectric conversion device are configured to detect light received from a light emitting device subsequently to the light irradiating a blood vessel, wherein each separate unit pixel of the plurality of unit pixels of the pulse oximeter-embedded near infrared organic image sensor includes a separate plurality of inorganic photoelectric conversion devices of the array of inorganic photoelectric conversion devices, the separate plurality of inorganic photoelectric conversion devices including a separate red inorganic photoelectric conversion device of the plurality of inorganic red photoelectric conversion devices, a separate blue inorganic photoelectric conversion device of the plurality of inorganic blue photoelectric conversion devices, and a separate green inorganic photoelectric conversion device of the plurality of inorganic green photoelectric conversion devices, and separate pixel electrodes of the array of pixel electrodes that are each overlapped with a separate inorganic photoelectric conversion device of the separate plurality of inorganic photoelectric conversion devices, a separate portion of the near infrared organic photoelectric conversion layer, and a separate portion of the common electrode.

4. The pulse oximeter-embedded near infrared organic image sensor of claim 3, further comprising:

a signal processor configured to calculate a heart rate and oxygen saturation using an absorbance of near infrared light that is measured by the near infrared organic photoelectric conversion device based on at least a portion of the received light in the particular near infrared wavelength spectrum being absorbed by the near infrared organic photoelectric conversion device, and an absorbance of red light that is measured by the plurality of inorganic red photoelectric conversion devices based on at least a portion of the received light in the particular red wavelength spectrum being absorbed by the plurality of inorganic red photoelectric conversion devices.

5. A wearable pulse oximeter, comprising:

a light emitting device configured to emit white light having an intensity of about 1 to about 10 mW; and a sensor including a stack of a near infrared organic photoelectric conversion device and an array of inorganic photoelectric conversion devices, the near infrared organic photoelectric conversion device configured to sense a particular near infrared wavelength spectrum of light, the array of inorganic photoelectric conversion devices overlapping separate portions of the near infrared organic photoelectric conversion device, the array of inorganic photoelectric conversion devices including a red inorganic photoelectric conversion device configured to sense a particular red wavelength spectrum of light, a blue inorganic photoelectric conversion device configured to sense a particular blue wavelength spectrum of light, and a green inorganic photoelectric conversion device configured to sense a particular green wavelength spectrum of light.

6. The wearable pulse oximeter of claim 5, further comprising:
a signal processor configured to calculate a heart rate and oxygen saturation using
an absorbance of near infrared light that is measured by the near infrared organic photoelectric conversion device based on at least a portion of incident light in the particular near infrared wavelength spectrum being absorbed by the near infrared organic photoelectric conversion device, and
an absorbance of red light that is measured by the red inorganic photoelectric conversion device based on at least a portion of the incident light in the particular red wavelength spectrum being absorbed by the red inorganic photoelectric conversion device.

7. The wearable pulse oximeter of claim 5, further comprising:
a flexible display configured to display a signal of the sensor.

8. An angiographic device, comprising:
a light emitting device configured to emit white light having an intensity of about 1 to about 10 mW to irradiate a blood vessel;
a near infrared organic photoelectric conversion device including a near infrared organic photoelectric conversion layer on a semiconductor substrate, a common electrode on the near infrared organic photoelectric conversion layer, and a plurality of pixel electrodes between the near infrared organic photoelectric conversion layer and the semiconductor substrate; and
an array of inorganic photoelectric conversion devices embedded in the semiconductor substrate and overlapping separate pixel electrodes of the near infrared organic photoelectric conversion device, separate portions of the near infrared organic photoelectric conversion layer, and separate portions of the common electrode,
wherein the array of inorganic photoelectric conversion devices includes
a red inorganic photoelectric conversion device configured to sense a particular red wavelength spectrum of light,
a blue inorganic photoelectric conversion device configured to sense a particular blue wavelength spectrum of light, and
a green inorganic photoelectric conversion device configured to sense a particular green wavelength spectrum of light, and
wherein the inorganic red photoelectric conversion device is configured to sense the particular red wavelength spectrum of light of transmitted light that is received from the light emitting device, subsequently to the transmitted light having irradiated the blood vessel, and the near infrared organic photoelectric conversion device is configured to sense a particular near infrared wavelength spectrum of light of the transmitted light.

9. The angiographic device of claim 8, further comprising:
a signal processor configured to calculate a heart rate and oxygen saturation using
an absorbance of near infrared light that is measured by the near infrared organic photoelectric conversion device based on at least a portion of the transmitted light in the particular near infrared wavelength spectrum being absorbed by the near infrared organic photoelectric conversion device, and
an absorbance of red light that is measured by the of inorganic red photoelectric conversion device based on at least a portion of the transmitted light in the particular red wavelength spectrum being absorbed by the inorganic red photoelectric conversion device.

10. A smart phone, comprising:
a light emitting device configured to emit white light to irradiate a blood vessel; and
a pulse oximeter-embedded near infrared organic image sensor configured to detect transmitted light transmitted from the light emitting device, subsequently to the transmitted light having irradiated the blood vessel, the pulse oximeter-embedded near infrared organic image sensor including
an array of inorganic photoelectric conversion devices embedded in a semiconductor substrate and at least partially defining a plurality of unit pixels, the array of inorganic photoelectric conversion devices including a plurality of inorganic red photoelectric conversion devices configured to sense a particular red wavelength spectrum of light, a plurality of inorganic blue photoelectric conversion devices configured to sense a particular blue wavelength spectrum of light, and a plurality of inorganic green photoelectric conversion devices configured to sense a particular green wavelength spectrum of light,
a near infrared organic photoelectric conversion layer on the array of inorganic photoelectric conversion devices embedded in the semiconductor substrate, the near infrared organic photoelectric conversion layer configured to absorb a particular near infrared wavelength spectrum of light,
a common electrode on the near infrared organic photoelectric conversion layer, and
an array of pixel electrodes between the near infrared organic photoelectric conversion layer and the semiconductor substrate,
wherein each separate unit pixel of the plurality of unit pixels of the pulse oximeter-embedded near infrared organic image sensor includes
a separate plurality of inorganic photoelectric conversion devices of the array of inorganic photoelectric conversion devices, the separate plurality of inorganic photoelectric conversion devices including
a separate red inorganic photoelectric conversion device of the plurality of inorganic red photoelectric conversion devices,
a separate blue inorganic photoelectric conversion device of the plurality of inorganic blue photoelectric conversion devices, and
a separate green inorganic photoelectric conversion device of the plurality of inorganic green photoelectric conversion devices, and
separate pixel electrodes of the array of pixel electrodes that are each overlapped with a separate inorganic photoelectric conversion device of the separate plurality of inorganic photoelectric conversion devices,
a separate portion of the near infrared organic photoelectric conversion layer, and a separate portion of the common electrode.

11. The smart phone of claim 10, further comprising:
a signal processor configured to calculate a heart rate and oxygen saturation using
an absorbance of near infrared light that is measured by the pulse oximeter-embedded near infrared organic image sensor based on at least a portion of the transmitted light in the particular near infrared wavelength spectrum being absorbed by the near infrared organic photoelectric conversion layer, and an absorbance of red light that is measured by the pulse oximeter-embedded near infrared organic image sensor based on at least a portion of the transmitted light in the particular red wavelength spectrum being absorbed by the plurality of inorganic red photoelectric conversion devices.

12. A pulse oximeter, comprising:

a light emitting device configured to emit white light having an intensity of about 1 to about 10 mW; and a sensor configured to detect at least a particular limited wavelength portion of the white light that is emitted by the light emitting device, the sensor including a near infrared organic photoelectric conversion device on a semiconductor substrate, the near infrared organic photoelectric conversion device configured to sense a particular near infrared wavelength spectrum of light, and an array of inorganic photoelectric conversion devices embedded in the semiconductor substrate, the array of inorganic photoelectric conversion devices including a red inorganic photoelectric conversion device configured to sense a particular red wavelength spectrum of light, a blue inorganic photoelectric conversion device configured to sense a particular blue wavelength spectrum of light, and a green inorganic photoelectric conversion device configured to sense a particular green wavelength spectrum of light, wherein each separate inorganic photoelectric conversion device of the array of inorganic photoelectric conversion devices is overlapped with a separate portion of the near infrared organic photoelectric conversion device.

13. The pulse oximeter of claim 12, further comprising:

a signal processor configured to calculate a heart rate and oxygen saturation based on a determination of an absorbance of near infrared light that is measured by the near infrared organic photoelectric conversion device based on at least a portion of the white light that is emitted by the light emitting device in the particular near infrared wavelength spectrum being absorbed by the near infrared organic photoelectric conversion device, and an absorbance of red light that is measured by the red inorganic photoelectric conversion device based on at least a portion of the white light that is emitted by the light emitting device in the particular red wavelength spectrum being absorbed by the red inorganic photoelectric conversion device.

* * * * *